United States Patent [19]

McArdle et al.

[11] Patent Number: 5,084,490

[45] Date of Patent: Jan. 28, 1992

[54] STYRYLOXY COMPOUNDS AND POLYMERS THEREOF

[75] Inventors: Ciaran B. McArdle; Joseph Burke, both of Dublin, Ireland; John G. Woods, Farmington, Conn.

[73] Assignee: Loctite (Ireland) Limited, Dublin, Ireland

[21] Appl. No.: 625,725

[22] Filed: Dec. 10, 1990

[51] Int. Cl.$^5$ .................. C08F 2/46; C08F 12/24; C07C 41/00
[52] U.S. Cl. ................... 522/181; 526/313; 568/654; 568/657
[58] Field of Search .............. 522/181; 526/313; 568/654, 657

[56] References Cited

U.S. PATENT DOCUMENTS 4,543,397  9/1985  Woods et al. ............... 526/313
4,732,956  3/1988  Woods et al. ............... 526/260

Primary Examiner—Marion E. McCamish
Assistant Examiner—Mark A. Chapman
Attorney, Agent, or Firm—Edward K. Welch, II; Eugene F. Miller

[57] ABSTRACT

Styryloxy compounds of the formula IV

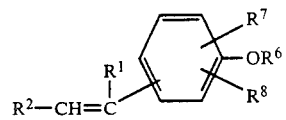

wherein $R^1$ and $R^2$ are H, or one of $R^1$ and $R^2$ is H and the other is methyl;

$R^7$ and $R^8$ (which may be the same or different) are H, $C_1$–$C_5$ alkyl or $C_1$–$C_5$ alkenyl; or one of $R^7$ and $R^8$ may be —$OR^6$ or $C_1$–$C_5$ alkoxy or $C_1$–$C_5$ alkenyloxy if $R^2$ is not methyl;

$R^6$ is selected from the group consisting of:

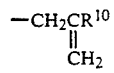

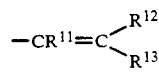

where $R^{10}$ is $C_1$–$C_5$ alkyl; and $R^{11}$, $R^{12}$ and $R^{13}$, which may be the same or different, are H or $C_1$–$C_5$ alkyl, are described as new low viscosity liquid styryloxy monomers which can be photocured and which form transparent polymers. They have an advantageous effect in a mixture with 4-allyloxystyrene, and this mixture has a synergistic effect in combination with divinyl ethers of a polyalkylene oxide.

20 Claims, No Drawings

STYRYLOXY COMPOUNDS AND POLYMERS THEREOF

CROSS REFERENCE TO RELATED APPLICATIONS

This Application is related to application Ser. No. 07/625,574 filed on even date herewith entitled "A Method of Forming High-Temperature Resistant Polymers" (McArdle et al).

BACKGROUND OF THE INVENTION

1. Field of the Invention

This invention relates to difunctional styryloxy compounds which are cationically polymerizable, and to polymers thereof, particularly for use in surface coatings, films, inks, adhesives, sealants and the like.

2. Description of the Related Art

U.S. Pat. No. 4,543,397 Woods et. al., describes polyfunctional cationically polymerizable styryloxy compounds of the formula I or II

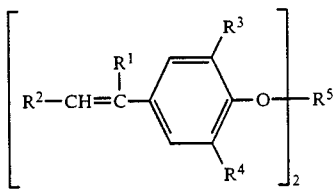

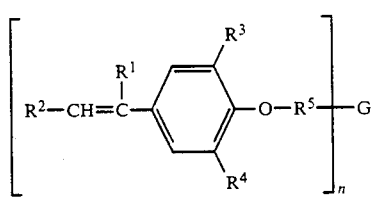

where $R^1$ and $R^2$ are H, or one of $R^1$ and $R^2$ is H and the other is methyl; $R^3$ and $R^4$ are H, lower alkyl or alkoxy if $R^2$ is not methyl; $R^5$ is a divalent hydrocarbon radical; G is a multivalent organic or inorganic radical free of amine, aliphatic hydroxyl, aliphatic thiol or other groups which interfere with cationic polymerization; and n is an integer of two or more.

Polyfunctional telechelic styryloxy monomers of the kind described in U.S. Pat. No. 4,543,397 are generally of high molecular weight. Even so, example 10 of that Patent describes the preparation of 4-allyloxystyrene of the formula III

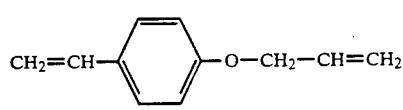

This compound is cationically active but it forms linear polymers which are purple/blue in color and only 10% insoluble in organic solvents i.e. little if any crosslinking has occurred.

SUMMARY OF THE INVENTION

It is an object of the present invention to provide simple low viscosity liquid styryloxy monomers which can be crosslinked and which form transparent polymers.

The invention provides styryloxy compounds of the formula IV

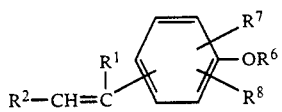

wherein $R^1$ and $R^2$ are H, or one of $R^1$ and $R^2$ is H and the other is methyl; $R^7$ and $R^8$ (which may be the same or different) are H, $C_1$–$C_5$ alkyl or $C_1$–$C_5$ alkenyl; or one of $R^7$ and $R^8$ may be —$OR^6$ or $C_1$–$C_5$ alkoxy or $C_1$–$C_5$ alkenyloxy if $R^2$ is not methyl;

$R^6$ is selected from the group consisting of:

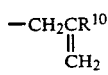

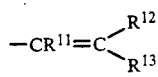

where $R^{10}$ is $C_1$–$C_5$ alkyl; and $R^{11}$, $R^{12}$ and $R^{13}$, which may be the same or different, are H or $C_1$–$C_5$ alkyl.

Preferably at least one of $R^{11}$, $R^{12}$ and $R^{13}$ is $C_1$–$C_5$ alkyl.

In one preferred embodiment, $R^{11}$ is H and $R^{12}$ and $R^{13}$ are both $C_1$–$C_5$ alkyl. In another preferred embodiment, $R^{11}$ and $R^{12}$ are H, and $R^{13}$ is $C_1$–$C_5$ alkyl.

A preferred group of compounds within the scope of the present invention are those wherein the styryl moiety ($R^2CH=C(R^1)$—) is para to the —$OR^6$ moiety. In such compounds, it is also further preferred that at least one position ortho to the —$OR^6$ moiety is unsubstituted, i e., H. Especially preferred compounds are those wherein $R^1$, $R^2$, $R^7$ and $R^8$ are H.

The most preferred compounds are of the formula V

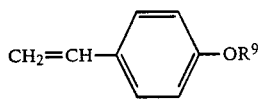

wherein $R^9$ is selected from the group consisting of:

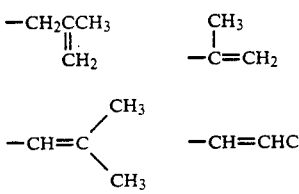

The compounds of the present invention are monofunctional with respect to the styryl group but are difunctional because of the other cationically active substituent —$OR^6$. They are compatible with photoinitiators, which are soluble therein, and they can be photocured to give highly transparent polymeric films with good mechanical properties after short irradiation times e.g. 10 seconds or less. Thus, low viscosity monomers may be converted to strong crosslinked polymers.

In one aspect therefore, the present invention provides a polymerizable composition comprising a styryloxy compound of formula IV together with a photoinitiator.

The compounds of the present invention may also be used as reactive diluents e.g. in epoxy resins, vinyl ether resins, styryloxy resins, etc. As reactive diluents, these compounds may co-react with the other constituent(s) or they may react concurrently with the polymerization of the co-constituent(s).

The compounds of the present invention are especially useful as co-constituents in combination with other styryloxy monomers. Additionally, they have a particularly surprising effect in admixture with 4-allyloxystyrene (formula III) in that the addition of even small percentages of one of the compounds of formula IV to 4-allyloxystyrene produces a monomer mixture which polymerizes to a transparent insoluble film.

The present invention therefore also provides a polymerizable composition comprising 4-allyloxystyrene of formula III in admixture with a styryloxy compound of formula IV as defined herein, together with a photoinitiator. In general, the styryloxy compound of formula IV is present in an amount of at least 1% by weight, preferably in the range of from about 2.5% to about 35% by weight, most preferably in the range of from about 3% to about 10% by weight based on the combined weight of the allyloxystyrene and the styryloxy compound of formula IV.

It has also surprisingly been found that a synergistic effect is achieved by combining an admixture of 4-allyloxystyrene and a styryloxy compound of formula IV with a vinyl ether monomer, specifically a divinyl ether of a polyalkylene oxide e.g. the divinyl ether of triethylene oxide.

In a further aspect therefore the present invention provides a photopolymerizable composition comprising:

(A) a styryloxy component selected from the group consisting of:
(i) 4-allyloxystyrene,
(ii) at least one styryloxy compound of formula IV as defined above, and
(iii) a mixture of (i) and (ii),
(B) a divinyl ether of a polyalkylene oxide and
(C) a photoinitiator, the ratio of (A):(B) being in the range from 1:9 to 20:1.

Preferably the ratio of (A) to (B) is in the range 2:1 to 9:1, more preferably 1:1 to 4:1, most preferably about 3:1.

It is especially preferred that the styryloxy component (A) be a mixture (iii) of the allyloxy styrene (i) and styryloxy compound of formula IV (ii). Within said mixture, the ratio of (i) to (ii) is preferably in the range 20:1 to 1:2, more particularly 7.5:1 to 2:1, especially about 6:1 to 3:1. These ratios are calculated without reference to any small amounts of other components.

The divinyl ether of a polyalkylene oxide preferably is of the formula $CH_2=CH\text{-}[O\text{---}(CH_2)_n\text{---}O]_m\text{CH}=CH_2$, wherein n=1-6 (preferably n=2) and m is greater than or equal to 2 (preferably m=2-10). The preferred compound is the divinyl ether of triethylene oxide, which is commercially available.

Although any of the individual compounds above as well as combinations of A(i) or A(ii) with (B) provide cured compositions with excellent properties, the synergistic combination A(iii) and mixtures thereof with B have been found to manifest superior properties, particularly as regards bond strength.

The photoinitiator may be any suitable UV cationic initiator. Such UV cationic photoinitiators include salts of a complex halogenide having the formula:

$$[A]_b^+ [MX_e]^{-(e-f)}$$

where A is a cation selected from the group consisting of iodonium, sulfonium, pyrylium, thiopyrylium and diazonium cations, M is a metalloid, and X is a halogen radical, b equals e minus f, f equals the valence of M and is an integer equal to from 2 to 7 inclusive, e is greater than f and is an integer having a value up to 8. Examples include di-p-tolyl iodonium hexafluorophosphate, diphenyl iodonium hexafluorophosphate, diphenyl iodonium hexafluoroarsenate and UVE (or GE) 1014 (trademark of General Electric), a commercially available sulfonium salt of a complex halogenide.

The precise mechanism or mechanisms by which the compounds of the present invention homopolymerize and/or copolymerize, as appropriate, to form a substantially insoluble crosslinked polymer is not known. Although not intending to be bound by any particular theory, it is believed that occurs through the unsaturation in the oxy (—$OR^6$ or —$OR^9$) moiety. Specifically, it is believed that the oxy mo may crosslink between pendant oxy moieties of other styryloxy monomers or between pendant oxy moiety and free styryl moiety ($R^2CH=C(R^1)$—) as well. In compositions comprising other co-constituents, e.g., 4-allyloxystyrene and/or divinyl ether, the crosslinking will also occur by a co-reaction between the styryl or oxy moieties of the styryloxy compounds of formula IV with co-reactive sites on the co-constituent.

Furthermore, although it is believed that there may be some minor degree of a photoinduced claisen-type rearrangement in the styryloxy compounds of formula IV, it is not believed that the resultant monomers participate to a large extent, if at all, in the concurrent photo induced crosslinking reaction. This claisen-type rearrangement does, however, play an important role in a subsequent heat treatment step as described in the aforementioned co-filed patent application of McArdle et al.

DESCRIPTION OF THE PREFERRED EMBODIMENTS

The invention may be illustrated by reference to the following non-limiting examples, in which all percentages are by weight unless otherwise indicated.

4-Isobutenyloxystyrene

4-Ethyl acetoxy benzaldehyde was prepared by the reaction of one mole of ethyl bromoacetate with one mole of 4-hydroxy benzaldehyde in the presence of one mole of anhydrous Potassium Carbonate in refluxing acetone. This precursor material was vacuum distilled after filtration and concentration of the reaction mixture. The precursor boiled in the range 138°-140° C. at 0.2 mbar and appeared as a slightly yellowish liquid which crystallized on standing.

4-Isobutenyloxystyrene was prepared from 4-ethyl acetoxy benzaldehyde by Wittig reduction. Thus to Methyl triphenyl phosphonium bromide (205.6 g, 0.576 mole) in anhydrous tetrahydrofuran and under a nitrogen atmosphere, was added Sodium Amide (26 g, 0.576 mole plus excess to account for its 90% strength). The mixture was stirred at room temperature and became slightly yellow after 30 minutes. After 3½ hours of stirring the mixture was deep yellow and 4-ethylacetoxy benzaldehyde (60 g, 0.288 mole) was added portionwise. When the addition was complete, the mixture had turned a deep tan color. The mixture was further refluxed for 2-3 hours. On cooling and filtering, the reaction mixture was concentrated and continuously extracted with 40°-60° C. bp petroleum ether in which reaction by-product triphenylphosphine oxide is sparingly soluble, whereas the desired product has high solubility. On concentration of the extracts a yellow-brown oil resulted, 10 g of which subjected to vacuum distillation. Three fractions resulted which has the following characteristics:

Fraction (1): bp~150° C. @0.3 mbar; IR (Key bands) split C=O stretch (1760, 1735 cm$^{-1}$, weak), olefinic=-C—H stretch (1660 cm$^{-1}$ weak), conjugated olefinic=-C—H (1625 cm$^{-1}$ medium).

Fraction (2): bp~170° C. @0.3 mbar; IR (Key bands) as for (1) with more intense C=O bands and an ill defined ester pattern —C(O)—O— (1220-1240 cm$^{-1}$).

Fraction (3): bp~195° C. @0.3 mbar; IR (Key bands), —CH stretch [2995 (asym.), 2800 (sym) cm$^{-1}$], split C=O (1760, 1735 cm$^{-1}$ intense), conjugated olefin (only) (1625 cm$^{-1}$, med.), characteristic (1205-1240 cm$^{-1}$, intense). The ratio for Fraction 1:2:3 was 11:3:1.

Fraction 1 was further purified by spinning plate preparative thin layer chromatography with 40°-60° C. bp petroleum ether as eluant. Six grammes of a water clear low viscosity liquid with a characteristic aniseed smell were thus isolated which was 100% pure by HPLC. GC-MS evidence confirmed a molecular weight of 174; the major abundances from the fragmentation pattern were 159, 120, 91, 77, 65, 55 and 39 m/g$^z$. High field H' N.M.R. (CDCl$_3$; TMS) assignments were as follows:

| 2H | d 7.33 ppm | } | H$_5$, 5$^1$, 6, 6$^1$, J$_{5,6}$ = 8.5 H$_z$ |
| 2H | d 6.90 ppm | | |
| 1H | dd 6.65 ppm | | H$_7$, J$_{7,8}$ = 17 H$_z$; J$_{7,9}$ = 17 H$_z$ |
| 1H | dd 5.60 ppm | | H$_9$, J$_{9,7}$ = 17 H$_z$; J$_{9,8}$ = 1 H$_z$ |
| 1H | dd 5.10 ppm | | H$_8$ |
| 2H | Septet 4.95 ppm | | H$_{2,1}$ |
| 2H | S 4.36 ppm | | H$_{4,3}$ |
| 3H | S 1.78 ppm | | Me$_1$ |

The cationically active monomer 4-isobutenyloxystyrene when formulated with the commercially available cationic photoinitiators known as UVE (or GE) 1014 or alternatively Degacure(®) K126 (the former being products of General Electric Company whilst the latter is a Degussa material) at levels typically of 15 μl initiator per gramme of monomer, gave compatible clear compositions of low viscosity which photocured in 5 seconds at 100 mW/cm$^2$ exposure at predominantly 366 nm to give tack free clear and colorless films with high gloss and flexibility. These films showed a minimum of 75% insolubility after room temperature photocure in repeated solvent extractions over 24 hours with solvents such as toluene, CH$_2$Cl$_2$ and DMSO.

Photocured films (at room temperature) had a glass transition temperature (Tg) at 55° C. with a maximum Tan δ amplitude of 0.42 and a dynamic modulus E'≧562 MPa at temperatures of 50° C. to −100° C., the last data being measured by Dynamic Mechanical Thermal Analysis (DMTA) at a frequency of 1 Hz. Photocured films at elevated temperature (50° C.) show Tg at 67° C. with similar modulus performance.

An alternative procedure for the direct introduction of isobutenyl groups into phenols employs methylallyl chloride as a reagent (cf. Bartz, Miller and Adams, J. Am Chem Soc. 57, 371, 1935). Thus the Wittig reduction and isobutenyl formation may be separated into two steps by using 4-isobutenyloxy benzaldehyde as a substrate in place of 4-ethyl acetoxy benzaldehyde.

2-Methylpropenyloxystyrene

A saturated methanolic KOH solution was prepared, 15 g. of which was charged into a round bottom flask. To the saturated solution was added approximately 5 g of 4-isobutenyloxystyrene (Example 1) and the mixture was heated and stirred for 6 hours at 110° C., during this time the upper liquid layer turned from yellow to pink. On cooling, the upper liquid layer was easily drawn off from the solid bottom layer and the former was vacuum distilled, boiling in the range 52°-60° C. at 0.1 mbar. The distillate was a water clear low viscosity liquid with a characteristic aniseed smell. IR analysis indicated the presence of an intense 1670 cm$^{-1}$ band characteristic of β-substituted vinyl ethers and not present in the parent monomer (Example 1) and also the 960 cm$^1$ band due to, CH wag in substituted vinyl ethers. High resolution H' NMR (CDCl$_3$; TMS) gave the following assignments:

| 2H | d 7.33 ppm | } | H$_{2,21,3,31}$, J$_{2,3}$ = 8.5 H$_z$ |
| 2H | d 6.90 ppm | | |
| 1H | dd 6.65 ppm | | H$_4$, J$_{4,5}$ = 11 H$_z$ J$_{4,6}$ = 17 H$_z$ |
| 1H | septet 6.20 ppm | | H$_1$, J$_1$, Me = 1 H$_z$ |
| 1H | dd 5.60 ppm | | H$_6$, J$_{4,6}$ = 17 H$_z$ J$_{5,6}$ = 1 H$_z$ |
| 1H | dd 5.10 ppm | | H$_5$ |
| 6H | 2Xd 1.70 ppm; | | Me J$_1$, Me = 1 H$_z$ |

This monomer was cationically active as before, curing tack free i 10 seconds @100 mW/cm$^2$ @predominantly 366 nm. The resulting polymer was a flexible solid with a Tg of 85° C. (1 Hz by DMTA).

EXAMPLE 3

4-Allyloxystyrene 4-allyloxybenzaldehyde was prepared by reaction of allyl bromide on 4-hydroxybenzaldehyde in refluxing acetone in the presence of $K_2CO_3$. The distilled product was used as a precursor for 4-allyloxystyrene synthesis.

To approximately one liter of anhydrous THF and under a $N_2$ atmosphere was added 265 g (0.74 mole) of methyl triphenyl phosphonium bromide in a multi-necked flask equipped with an efficient mechanical stirrer. Sodium amide 93-97%, (approximately 0.74 mole) was added and stirring at room temperature continued for about three hours until a deep canary yellow color had formed. 4-allyloxybenzaldehyde (100 g, 0.62 mole) was then added gradually and the reaction mixture, now tan in color, was subsequently brought to reflux and maintained there for about four hours. The reaction was stopped when TLC analysis showed the aldehyde to be consumed. On cooling the filtrate was extracted with 40°-60° C. bp petroleum ether until HPLC analysis showed that less than 40% of the contents was by-product triphenyl phosphine oxide. The concentrated extracts at that stage were subjected to vacuum distillation yielding a water clear liquid of low viscosity, bp≅50° C. at 0.6 mbar, with a characteristic aniseed smell.

Analysis by GC-MS indicated the liquid to contain two components, a lower boiling component present at 3% and a higher boiling component at 97%. Both were isomeric materials of 160 mass units by MS analysis. The major component was identified as 4-allyloxystyrene by $^1H$ 270 MHz NMR analysis, IR analysis and GC-MS analysis following separation of a sample of the distillate by preparative TLC. The minor component was identified, by the same techniques and from the same isolation procedure, as 4-propenyloxystyrene (see Example 4).

EXAMPLE 4

4-Propenyloxystyrene

This material was prepared by base catalyzed isomerization of 4-allyloxystyrene using saturated methanolic KOH in the same way as described in Example 2 (6 hours, 150° C). IR analysis indicated intense 1670 $cm^{-1}$ absorption due to β-substituted vinyl ether with concomitant disappearance of the 1640 $cm^{-1}$ allyl olefinic signal present in the precursor, again a strong 960 $cm^{-1}$ absorbance was noted in the new molecule. The pure material was prepared by vacuum distillation boiling at 48° C. at 0.3 mbar (cf. 60° C. @0.3 mbar for 4-alloxystyrene). GC-MS analysis confirmed a molecular weight of 160 with major m/z peaks at 120, 91, 77, 65, 39. High resolution $^1H$ NMR (CDCl$_3$; TMS) gave the following assignments:

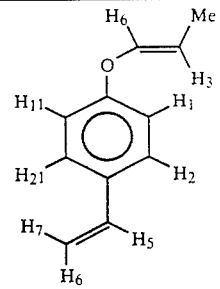

| 2H | d 7.37 ppm | $H_{2,21}, J_{1,2} = 8.5\ Hz$ |
|---|---|---|
| 2H | d 6.95 ppm | $H_1, 1^1$ |
| 1H | dd 6.65 ppm | $H_5, J_{5,6} = 11.0\ Hz$ |
| | | $J_{5,7} = 18.0\ Hz$ |
| 1H | dq 6.40 ppm | $H_3, J_{3,4} = 6.0\ Hz$ |

-continued

| | | |
|---|---|---|
| | | $J_{B,Me} = 1.5\ Hz$ |
| 1H | dd 5.60 ppm | $H_7, J_{6,7} = 1.0\ Hz$ |
| | | $J_{5,7} = 18\ Hz$ |
| 1H | dd 5.15 ppm | $H_6, J_{5,6} = 11\ Hz$ |
| | | $J_{6,7} = 1.0\ Hz$ |
| 1H | dq 5.40 ppm | $H_4, J_{3,4} = 6.0\ Hz$ |
| | | $J_{4,Me} = 8.0\ Hz$ |
| 3H | dd 1.70 ppm | Me. |

An alternative method of synthesis involves reaction of 1-bromo-1-propene with 4-hydroxybenzaldhyde in basic conditions followed by Wittig reduction of the reaction product.

The monomer was cationically active, photocuring tack free in about 5 seconds at room temperature when formulated with the photoinitiators mentioned in Example 1. The monomer is compatible with the said photoinitiators giving clear solutions with characteristic aniseed like smell.

EXAMPLE 5

Compositions which photocure cationically to give tack free insoluble films were prepared, starting with the mixture produced in Example 3 i.e. 97% 4-allyloxystyrene and 3% 4-propenyloxystyrene, and increasing the proportion of the propenyl compound up to 100% propenyl compound. The photoinitiator(s) from Example 1 were also present at about 1% level. The presence of the propenyloxystyrene transforms the properties of cationically active allyloxystyrene in that even at 3% level of 4-propenyloxystyrene crosslinking occurs and colorless largely insoluble films result. Without propenyloxystyrene, highly colored soluble linear polymers from cationically active allyloxystyrene result. Thus polymer films photocured from monomer mixtures such as 97% 4-allyloxystyrene and 3% 4-propenyloxystyrene or 91% 4-allyloxystyrene and 9% 4-propenyloxystyrene gave 90% insoluble residues in duplicated solvent extraction tests. Photocured films submitted to DMTA as in Example 1 had glass transition temperatures as follows:

| % 4-propenyloxystyrene | Tg |
|---|---|
| 0 | 62° C. |
| 3 | 75° C. |
| 9 | 87° C. |

The dynamic modulus E' for the crosslinked copolymers was 200 MPa to 60° C. from at least 10° C.; all DMTA data being quoted at 1 Hz.

As described above, the crosslinking resulting from the photopolymerization of the allyloxystyrene and propenyloxystyrene is believed to be largely due to the cationically active propenyloxy moiety of the 4-propenyloxystyrene. Generally, the styrenic portions of the two components will polymerize to form polystyrene-type chains having the respective allyloxy and propenyloxy moieties pendant thereto. The propenyloxy moiety will cationically crosslink with other propenyloxy moieties, as well as other pre-(non-reacted) styrenic ($CH_2=CH-$) moieties from either monomers. Although less active, it is also possible that the propenyloxy moiety may also crosslink with other pendant allyloxy moieties. In any event, as noted from the compositions of this Example 5, even low amounts of 4-propenyloxystyrene in the admixture results in a high degree of crosslinking as compared to 4-allyloxystyrene without the propenyloxystyrene.

EXAMPLE 6

A mixture of 4-allyloxystyrene and 4-propenyloxystyrene was prepared and analyzed by the GC-MS technique. The instrument used was a Hewlett-Packard 58-90 GC system with an electron impact mass selective detector. The column head pressure was 15 p.s.i. of Helium as carrier, column type was a 25 m capillary type of 0.25 mm with a BP10 coating. Injection was made at 300° C. from Analar (Trade Mark) grade chloromethane. Total ion current traces for the styryloxy mixture indicated three components to be present. Two components are isomeric and have molecular mass of 160 units. In order of ascending boiling points these two were identified as propenyloxystyrene and allyloxystyrene. The analysis also indicated the presence of a third compound referred to hereafter as K. The concentration of K in the gas chromatogram was dependent on the temperature of sample injection. Integration of GC data at 300° C. injection temperature characterized the styryloxy mixture as 22% propenyloxystyrene, 63% allyloxystyrene and 15% K. Proton NMR run at room temperature in $CDCl_3$ as solvent and TMS as reference indicated the styryloxy mixture to contain propenyloxystyrene and allyloxystyrene only.

Combinations of this styryloxy mixture with the divinyl ether of triethylene oxide known as DVE-3 commercially available from the GAF company, when formulated with the initiators described in Example 1, produced photocurable compositions which had superior properties to any of the individual components or to any mixtures outside of the optimized formulation range.

Pin-to-glass bond strengths for the respective compositions are summarized below (Table 1).

In Table 1, the following abbreviations are used:
DVE-3: Divinyl ether of triethylene oxide
$H_o$: Composition containing 75% of the styryloxy mixture with 25% of DVE-3.
HI: Composition containing 50% of the styryloxy mixture with 50% of DVE-3.
HII: Composition containing 25% of the styryloxy mixture with 75% of DVE-3.

All percentages being by weight.

It will be seen from Table 1, that composition $H_o$ gives the best results of all those tested and that the combination of styryloxy type monomers with DVE-3 at the optimized range gives performance much better than either of the styryloxy monomers alone or the DVE-3 alone.

TABLE 1

| Photocurable compositions containing 15 μl/gm GE1014 and exposed with 100 mW/cm² at predominantly 366 nm. | | | | |
|---|---|---|---|---|
| | Pin-to-Glass Bond Strength (dN per sq. cm.) after exposure for: | | | |
| Compound/ Formulation | 20 Seconds | 40 Seconds | 60 Seconds | Entry No. |
| Propenyloxystyrene | 14 | — | — | 1 |
| Allyloxystyrene | 12 | 12 | 13 | 2 |
| DVE-3 | 76 | 66 | 72 | 3 |
| Propenyloxystyrene: DVE-3 | | | | |
| at 75:25 | 59 | 57 | — | 4 |
| at 50:50 | 49 | 50 | — | 5 |
| at 25:75 | 69 | 57 | — | 6 |
| Allyloxystyrene: DVE-3 | | | | |
| at 75:25 | 87 | 84 | 80 | 7 |
| at 50:50 | 75 | 83 | 86 | 8 |
| at 25:75 | 72 | 79 | 90 | 9 |
| $H_o$ | 125 | 125 | 127 | 10 |
| $H_I$ | 95 | 103 | 87 | 11 |
| $H_{II}$ | 85 | 82 | 103 | 12 |

EXAMPLE 7

In Example 6 a synergistic improvement in bond strengths has been described for 75:25 styryloxy mixture: DVE-3 formulations containing photoinitiators. In the present example, the importance of the relative concentrations of various styryloxy isomers within the 75% styryloxy mixture content of the optimized formulation, is described.

In order to study the effect of varying the relative propenyloxystyrene and allyloxystyrene contents within the 75% styryloxy content photocurable compositions, a new batch of styryloxy monomers was prepared, characterized and modified. This batch of GC-MS analysis at 300° C. injection temperature indicated 22% propenyloxystyrene, 72% allyloxystyrene and 2% of K. The relative proportions of propenyloxystyrene and allyloxystyrene monomers were adjusted by addition of pure materials from separate stock so that nominally 50:50, 30:70, 20:80, 10:90 mixtures of propenyloxy to allyloxy monomers resulted, the K content never exceeded 2%. The said monomer mixtures then formed the 75% component of a mixture with DVE-3 (25%) together with photoinitiator. Pin-to-glass bond strengths were measured after photocuring with various exposure conditions. The results are summarized in Table 2 indicating that the optimum ratio of propenyloxy to allyloxy, is around 1:4.

TABLE 2

| Photocurable compositions containing 15 μl/gm GE1014 and exposed with 100 mW/cm² at predominantly 366 nm. | | | |
|---|---|---|---|
| | Relative improvement (%) in Pin-to-glass bond strength for various mixtures (taking Entry 1 as standard) after exposure for: | | Entry |
| Formulation: | 20 Seconds | 40 Seconds | No. |
| 37.5% propenyloxystyrene 37.5% allyloxystyrene 25% DVE-3 | 100 | 100 | 1 |
| 22.5% propenyloxystyrene 52.5% allyloxystyrene 25% DVE-3 | 129 | 111 | 2 |
| 15% propenyloxystyrene 60% allyloxystyrene 25% DVE-3 | 153 | 154 | 3 |
| 7.5% propenyloxystyrene | 140 | 145 | 4 |

TABLE 2-continued

Photocurable compositions containing 15 μl/gm GE1014 and exposed with 100 mW/cm² at predominantly 366 nm.

| Formulation: | Relative improvement (%) in Pin-to-glass bond strength for various mixtures (taking Entry 1 as standard) after exposure for: | | Entry No. |
|---|---|---|---|
| | 20 Seconds | 40 Seconds | |
| 67.5% allyloxystyrene 25% DVE-3 | | | 10 |

EXAMPLE 8

A further batch of styryloxy monomers was prepared and analyzed by the GC-MS technique at 300° C. injection temperature as 88% allyloxystyrene and 12% propenyloxystyrene only. The styryloxy monomer mixture was then formulated with DVE-3 in various proportions, together with photoinitiator pin-to-glass bond strengths were measured after photocuring for 20 seconds. The results are summarized in Table 3:

TABLE 3

Photocurable compositions containing 15 μl/gm GE1014 and exposed with 100 mW/cm² at predominantly 366 nm.

| Formulation DVE-3 | Styryloxy Mixture | Pin-to-Glass Bond Strengths (dN per sq. cm.) |
|---|---|---|
| 90% | 10% | 62 |
| 70% | 30% | 22* |
| 50% | 50% | 69 |
| 25% | 75% | 115 |

*Anomalous result

EXAMPLE 9

Another batch of styryloxy monomers was prepared and analyzed by the GC-MS Technique at 80% allyloxystyrene and 20% propenyloxystyrene only. A formulation consisting of 75% styryloxy monomer mixture, 25% DVE-3 and 15μl/gm$^{-1}$ GE1014 was photocured for 20 seconds at 100 mW/cm². Pin-to-glass bond strengths were measured and results in excess of 100 dN/sq. cm were obtained.

Certain of the photocured compositions produced as described above may be further crosslinked by treatment with heat to form high-temperature resistant polymers, as described in co-pending application Ser. No. 07/625,574 filed on even date herewith entitled "A Method of forming High-Temperature Resistant Polymers".

Obviously, other modifications and variations to the present invention are possible and may be apparent to those skilled in the art in light of the above teachings. Thus, it is to be understood that such modifications and variations to the specific embodiments set forth above are to be construed as being within the full intended scope of the present invention as defined by the appended claims.

We claim:

1. Styryloxy compounds of the formula IV

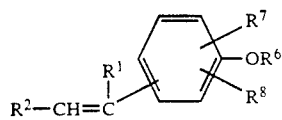

wherein $R^1$ and $R^2$ are H, or one of $R^1$ and $R^2$ is H and the other is methyl;

$R^7$ and $R^8$ (which may be the same or different) are H, $C_1-C_5$ alkyl or $C_1-C_5$ alkenyl; or one of $R^7$ and $R^8$ may be —OR$^6$ or $C_1-C_5$ alkoxyl or $C_1-C_5$ alkenyloxy if $R^2$ is not methyl;

$R^6$ is selected from the group consisting of:

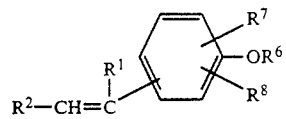

where $R^{10}$ is $C_1-C_5$ alkyl; and $R^{11}$, $R^{12}$ and $R^{13}$, which may be the same of different, are H or $C_1-C_5$ alkyl.

2. According to claim 1 wherein at least one of $R^{11}$, $R^{12}$ and $R^{13}$ is $C_1-C_5$ alkyl.

3. Compounds according to claim 1 wherein $R^1$, $R^2$, $R^7$ and $R^8$ are H.

4. Compounds according to claim 1 wherein the styryl moiety ($R^2CH=C(R^1)$—) is para to —OR$^6$.

5. Compounds according to claim 4 wherein at least one position ortho to —OR$^6$ is unsubstituted.

6. Compounds according to claim 1 which are of the formula V

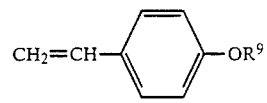

wherein $R^9$ is selected from the group consisting of:

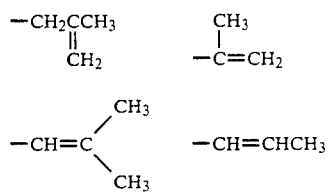

7. A polymerizable composition comprising a styryloxy compound of formula IV as defined in claim 1 together with a photoinitiator.

8. A polymerizable composition comprising 4-allyloxystyrene in admixture with a styryloxy compound of formula IV as defined in claim 1 together with a photoinitiator.

9. A composition according to claim 8 wherein the styryloxy compound of formula IV is present in an amount of from about 1 to about 99% by weight based on the combined weight of 4-allyloxystyrene and the styryloxy compound of formula IV.

10. A composition according to claim 8 wherein the styryloxy compound of formula IV is present in an amount of from about 2.5 to about 35% by weight based on the combined weight of 4-allyloxystyrene and the styryloxy compound of formula IV.

11. A composition according to claim 8 wherein the styryloxy compound of formula IV is present in an amount of from about 3 to about 10% by weight based on the combined weight of 4-allyloxystyrene and the styryloxy compound of formula IV.

12. A photopolymerizable composition comprising:

(A) a styryloxy component selected from the group consisting of
  (i) 4-allyloxystyrene,
  (ii) at least one styryloxy compound of formula IV as defined in claim 1 and
  (iii) a mixture of (i) and (ii) above,
(B) a divinyl ether of a polyalkylene oxide and
(C) a photoinitiator, the ratio of (A):(B) being in the range from 1:9 to 20:1.

13. A composition according to claim 12 wherein the ratio of (A):(B) is from 2:1 to 9:1.

14. A composition according to claim 12 where in the ratio of (A):(B) is from 1:1 to 4:1.

15. A composition, according to claim 12 wherein the styryloxy compound is a mixture (iii) of 4-allyloxystyrene (i) and a styryloxy compound of formula IV (ii).

16. A composition according to claim 15 wherein the ratio of (i):(ii) is from 20:1 to 1:2.

17. A composition according to claim 15 wherein the ratio of (i):(ii) is from 7.5:1 to 2:1.

18. A composition according to claim 15 wherein the ratio of (i):(ii) is from 6:1 to 3:1.

19. A composition according to claim 12 wherein the divinyl ether of a polyalkylene oxide is of the formula:

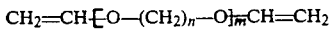

wherein n=1-6 and m is greater than or equal to 2.

20. A composition according to claim 19 wherein n is 2 and m is 2 to 10.

* * * * *

UNITED STATES PATENT AND TRADEMARK OFFICE
CERTIFICATE OF CORRECTION

PATENT NO. : 5,084,490
DATED : 28 January 1992
INVENTOR(S) : Ciaran B. McArdle, et al.

It is certified that error appears in the above—identified patent and that said Letters Patent is hereby corrected as shown below:

In claim 1, Column 12, line 9, delete

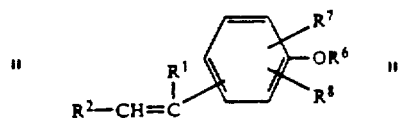

and insert therefor

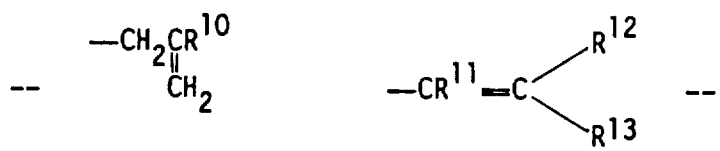

Signed and Sealed this

Eighth Day of March, 1994

*Attest:*

BRUCE LEHMAN

*Attesting Officer*  Commissioner of Patents and Trademarks